United States Patent
Geilen et al.

(10) Patent No.: US 11,174,207 B2
(45) Date of Patent: Nov. 16, 2021

(54) PROCESS FOR THE ISOMERIZATION OF OLEFINS

(71) Applicant: Evonik Operations GmbH, Essen (DE)

(72) Inventors: Frank Geilen, Haltern am See (DE); Felix Gärtner, Haltern am See (DE); Horst-Werner Zanthoff, Muelheim a.d. Ruhr (DE); Guido Stochniol, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/949,691

(22) Filed: Nov. 11, 2020

(65) Prior Publication Data
US 2021/0147320 A1 May 20, 2021

(30) Foreign Application Priority Data
Nov. 14, 2019 (EP) .................... 19209078

(51) Int. Cl.
*C07C 5/00* (2006.01)
*C07C 5/25* (2006.01)
*B01J 29/70* (2006.01)
*B01J 35/10* (2006.01)

(52) U.S. Cl.
CPC ............ *C07C 5/2518* (2013.01); *B01J 29/70* (2013.01); *B01J 35/1014* (2013.01); *B01J 35/1019* (2013.01); *C07C 2529/70* (2013.01)

(58) Field of Classification Search
CPC ... C07C 5/2512; C07C 11/08; C07C 2521/12; C07C 2529/70; C07C 5/2518; B01J 21/12; B01J 29/70; B01J 35/1014; B01J 35/1019; B01J 37/0009
See application file for complete search history.

(56) References Cited

U.S. PATENT DOCUMENTS

| 6,752,864 B2 | 6/2004 | Meyer et al. |
| 9,371,255 B2 | 6/2016 | Winterberg et al. |
| 2018/0208524 A1* | 7/2018 | Alshafei ................. C07C 4/06 |

FOREIGN PATENT DOCUMENTS

| DE | 101 23 950 | 11/2002 |
| WO | 2012/123292 | 9/2012 |

OTHER PUBLICATIONS

European Search Report dated May 14, 2020 in European Application No. 19209078.5.

* cited by examiner

*Primary Examiner* — Sharon Pregler
(74) *Attorney, Agent, or Firm* — Grüneberg and Myers PLLC

(57) ABSTRACT

A process is useful for the isomerization of $C_4$ to $C_9$ olefins having an internal double bond into the corresponding olefins having a terminal double bond using a heterogeneous catalyst system of a silicon-aluminium mixed oxide composition.

17 Claims, No Drawings

PROCESS FOR THE ISOMERIZATION OF OLEFINS

CROSS-REFERENCE TO RELATED APPLICATIONS

This application claims the benefit of European Application No. 19209078.5, filed on Nov. 14, 2019, the entirety of which is incorporated herein by reference.

BACKGROUND OF THE INVENTION

Field of the Invention

The present invention relates to a process for the isomerization of $C_4$ to $C_9$ olefins having an internal double bond to the corresponding olefins having a terminal double bond using a heterogeneous catalyst system that comprises a silicon-aluminium mixed oxide composition.

Description of the Related Art

In isomerizations (processes within a molecule are also referred to as rearrangements), the original molecule is converted into a molecule in which the empirical formula is unchanged, but the order or arrangement of the atoms or the arrangement of the bonds is altered. Isomers often have comparable bond energies, consequently interconversion can take place relatively freely. A distinction is made according to the type of conversion, for example bond isomerization, in which double bonds for example undergo rearrangement between C—C linkages (numerous bond isomerizations involving heteroatoms such as O, N, P and S are however also known to those skilled in the art), skeletal isomerization, in which linear compounds undergo rearrangement to branched ones, hydroisomerization, in which an alkane undergoes rearrangement to an isomeric alkane in the presence of hydrogen via an alkene intermediate, or cis/trans isomerization, in which the substituents of a double bond are rearranged. Isomerizations are often accelerated by acidic/basic catalysts. The catalyst properties, such as the strength of the acid/base centers, largely determine which of the isomerizations in a molecule takes place. The isomerization that is desired here is a bond isomerization.

Olefins having a terminal double bond, so-called alpha-olefins (for example 1-butene, 1-hexene or 1-octene), are important starting materials in the chemical industry for numerous processes, for example in hydroformylation for the production of aldehydes, in oligomerizations or in polymerizations. Olefins having a terminal double bond have the advantage over olefins having an internal double bond (for example 2-butene, 2-hexene or 2-octene) of having in some cases considerably higher reactivity in industrially operated processes. Moreover, the olefins having a terminal double bond are considerably more costly than the corresponding olefins having an internal double bond. On the other hand, there is also a demand in the chemical industries for olefins having an internal double bond.

The corresponding olefins having a terminal or internal double bond may be provided by various processes, for example cracking processes. Another possibility is the catalytic isomerization of olefins having an internal double bond to the corresponding olefins having a terminal double bond. The reverse isomerization to olefins having an internal double bond is also possible. The degree of conversion is in each case limited by the thermodynamic equilibrium. The catalytic isomerization to olefins having a terminal double bond is disclosed for example in EP 0 718 036 A1.

The catalysts used in the related art for the isomerization to olefins having a terminal double bond are usually catalysts having acid/base functionality and catalysts containing transition metals (the latter in some cases in the presence of hydrogen, which corresponds to a so-called hydroisomerization). Acid/base catalysts that are used include aluminosilicates doped with alkali metals and alkaline earth metals, appropriately exchanged zeolites or purely basic oxides (e.g. MgO).

SUMMARY OF THE INVENTION

The general problem of isomerization reactions is that the olefins undergoing isomerization are, on account of their double bond, reactive molecules, which means that side reactions can occur. An example is oligomerization, which can take place on an acidic catalyst system and occurs as a side reaction to the isomerization when using acidic catalysts. In order to prevent olefin oligomerization during the isomerization to olefins having a terminal double bond, a basic catalyst system or catalysts doped with alkali metals or alkaline earth metals are used by preference.

It was surprisingly found that, in a departure therefrom, it is also possible to use (weakly) acidic $SiO_2$-based catalysts having a certain aluminium oxide content, that is to say catalysts based for example on the silicon-aluminium mixed oxide compositions mentioned herein, which provide high activity in the isomerization allied with good product selectivity. Not only that, but oligomerization as a side reaction is virtually or completely absent.

The process according to the invention is accordingly a process for the isomerization of $C_4$ to $C_9$ reactant olefins having an internal double bond, preferably $C_4$ to $C_8$ reactant olefins having an internal double bond, more preferably $C_4$ to $C_6$ reactant olefins having an internal double bond, particularly preferably $C_4$ reactant olefins having an internal double bond, to product olefins having a terminal double bond using a heterogeneous catalyst, the catalyst comprising a silicon-aluminium mixed oxide composition.

The invention includes the following embodiments below:

1. Process for the isomerization of $C_4$ to $C_9$ reactant olefins having an internal double bond to product olefins having a terminal double bond using a heterogeneous catalyst, the catalyst being a silicon-aluminium mixed oxide composition having the following composition:
   a) 96% to 99.99% by weight of silicon oxide (calculated as $SiO_2$); and
   b) 0.01% to 4% by weight of aluminium oxide (calculated as $Al_2O_3$).
2. Process according to embodiment 1, wherein the catalyst has the following composition:
   a) 98.5% to 99.95% by weight of silicon oxide (calculated as $SiO_2$); and
   b) 0.05% to 1.5% by weight of aluminium oxide (calculated as $Al_2O_3$).
3. Process according to any of the preceding embodiments, wherein the silicon-aluminium mixed oxide composition has a BET surface area of 50 to 250 $m^2/g$, preferably 100 to 220 $m^2/g$.
4. Process according to any of the preceding embodiments, wherein the catalyst consists of shaped bodies produced from the silicon-aluminium mixed oxide composition in a forming process with the addition of binders and at least temporary auxiliaries.

5. Process according to any of the preceding embodiments, wherein the isomerization is carried out using a hydrocarbon mixture that comprises the reactant olefin to be isomerized and additionally already the product olefin, wherein the content of the product olefin is increased through isomerization.

6. Process according to any of the preceding embodiments, wherein the isomerization is carried out at a temperature of between 20° C. and 600° C., preferably between 100° C. and 500° C., more preferably between 200° C. and 450° C.

7. Process according to any of the preceding embodiments, wherein the gas hourly space velocity during the isomerization is from 2000 to 8000 $h^{-1}$, preferably from 2500 to 4000 $h^{-1}$.

8. Process according to any of the preceding embodiments, wherein the reactant olefins used are $C_4$ to $C_8$ reactant olefins having an internal double bond, preferably $C_4$ to $C_6$ reactant olefins having an internal double bond, more preferably $C_4$ reactant olefins having an internal double bond.

9. Process according to embodiment 8, wherein the reactant olefins used are cis- and/or trans-2-butene or hydrocarbon mixtures comprising these 2-butenes, and the product olefin having a terminal double bond is 1-butene.

10. Process according to any of the preceding embodiments, wherein the silicon-aluminium mixed oxide composition is predominantly or entirely present in the form of aggregated primary particles.

11. Process according to embodiment 10, wherein the silicon-aluminium mixed oxide composition is characterized in that the weight ratio $(Al_2O_3/SiO_2)_{surface}$ of the primary particles in the near-surface region is smaller than the weight ratio $(Al_2O_3/SiO_2)_{total}$ in the totality of the primary particles.

12. Process according to embodiments 10 or 11, wherein the silicon-aluminium mixed oxide composition is predominantly or entirely present in the form of aggregated primary particles in which
I) the weight ratio of $(Al_2O_3/SiO_2)_{total}$ in the totality of the primary particles is 0.002 to 0.05, preferably 0.003 to 0.015, more preferably 0.005 to 0.01; and
II) the weight ratio $(Al_2O_3/SiO_2)_{surface}$ of the primary particles in a near-surface layer having a thickness of 5 nm is less than in the totality of the primary particles.

13. Process according to any of the preceding embodiments, wherein the catalyst is completely crystalline, partly crystalline or X-ray amorphous.

14. Process according to embodiment 13, wherein the catalyst is X-ray amorphous.

DETAILED DESCRIPTION OF THE INVENTION

The silicon-aluminium mixed oxide composition used as catalyst may be produced by flame hydrolysis according to the process disclosed inter alia in DE 198 47 161 A1 or in EP 0 850 876 A1. In this so-called "co-fumed process", volatile silicon and aluminium compounds, e.g. silicon tetrachloride and aluminium trichloride, are sprayed into a hydrogen/oxygen or hydrogen/air gas flame, causing the silicon and aluminium compounds to be hydrolysed by the water evolved in the gas flame and resulting in the formation of the mixed oxide composition.

An alternative process likewise disclosed in the documents cited is the so-called doping process. In this process, an oxide, in this case e.g. silicon oxide, is produced in the gas flame from the corresponding volatile compound (e.g. silicon tetrachloride) by flame hydrolysis in tandem with the introduction into the gas flame of an aerosol containing a salt of the element to be doped, in this case e.g. aluminium, resulting in the formation of the corresponding mixed oxide. The silicon-aluminium mixed oxide composition thus produced by flame hydrolysis is predominantly to entirely amorphous.

The silicon-aluminium mixed oxide composition produced by means of the production processes mentioned by way of example is characterized by its high chemical purity and preferably has the following composition:
a) 96% to 99.99% by weight of silicon oxide, preferably 98.5% to 99.95% by weight of silicon oxide (calculated as $SiO_2$); and
b) 0.01% to 4% by weight of aluminium oxide, preferably 0.05% to 1.5% by weight of aluminium oxide (calculated as $Al_2O_3$).

In a preferred embodiment of the present invention, the silicon-aluminium mixed oxide composition additionally contains alkali metal oxides and/or alkaline earth metal oxides, particularly preferably in an amount of up to 1% by weight based on the total composition.

In order to introduce the alkali metal oxides or alkaline earth metal oxides, the mixed oxide composition produced by flame hydrolysis may be treated with an aqueous solution of the alkali metal hydroxide or alkaline earth metal hydroxide. This can be done for example by wetting or impregnating the mixed oxide composition produced by flame hydrolysis with a solution of the alkali metal salt and/or alkaline earth metal salt. The treated mixed oxide composition is then washed with water, dried at 100 to 150° C. and calcined at 300 to 600° C., preferably at 450 to 550° C. Silicon and aluminium oxides may already contain traces of alkali metals or alkaline earth metals, which are not taken into account here.

The silicon-aluminium mixed oxide compositions of the present invention may additionally be treated with an acidic aqueous solution containing a phosphorus source. The phosphorus source used may be phosphoric acid, phosphonic acid, phosphinic acid, polyphosphoric acid or dihydrogen phosphate, preferably phosphoric acid. For this, the mixed oxide composition is first suspended in water and the resulting suspension then treated with the phosphorus source, preferably such that the pH is within a range from 0 to 6, more preferably within a range from 1 to 2.5, particularly preferably within a range from 2 to 2.5. The treated mixed oxide composition is then washed with water, dried at 100 to 150° C. and calcined at 300 to 600° C., preferably at 450 to 550° C.

In a preferred embodiment, the silicon-aluminium mixed oxide composition according to the invention is predominantly (i.e. >70%) or entirely present in the form of aggregated primary particles. The silicon-aluminium mixed oxide composition is characterized here inter alia in that the weight ratio $(Al_2O_3/SiO_2)_{surface}$ of the primary particles in the near-surface region is smaller than the weight ratio $(Al_2O_3/SiO_2)_{total}$ in the totality of the primary particles. The term "near-surface region" refers to the region from the surface down to a depth of 5 nm. The difference in the weight ratios means that the aluminium oxide concentration at the surface is lower than in the overall composition. The totality of the primary particles includes the silicon dioxide and aluminium oxide fraction in the near-surface region.

Preference is therefore given to a silicon-aluminium mixed oxide composition that is predominantly or entirely present in the form of aggregated primary particles in which
I) the weight ratio $(Al_2O_3/SiO_2)_{total}$ in the totality of the primary particles is 0.002 to 0.05, preferably 0.003 to 0.015, more preferably 0.005 to 0.01; and
II) the weight ratio $(Al_2O_3/SiO_2)_{surface}$ of the primary particles in the near-surface region is lower than in the totality of the primary particles.

The weight ratio $(Al_2O_3/SiO_2)_{surface}$ at the surface may be determined for example by X-ray-induced photoelectron spectroscopy (XPS analysis) of the powder. Additional information about the surface composition may be determined by energy-dispersive X-ray analysis (TEM-EDX analysis) of individual primary particles. The weight ratio $(Al_2O_3/SiO_2)_{total}$ in the totality of the primary particles may be determined by chemical or physicochemical methods, e.g. X-ray fluorescence analysis, on the powder.

The silicon-aluminium mixed oxide composition used as a catalyst in the present invention may be X-ray amorphous, have crystalline fractions (partly crystalline) or be completely crystalline. The silicon-aluminium mixed oxide composition used as a catalyst is preferably X-ray amorphous. X-ray amorphous in the context of the present invention means that an X-ray amorphous substance exhibits no crystalline structure in the X-ray diffractogram down to the detection limit of 5 nm.

The described silicon-aluminium mixed oxide composition according to the invention, in particular having the composition stated above and in particular having the stated differences in the weight ratios $(Al_2O_3/SiO_2)$, preferably has a BET surface area of 50 to 250 m$^2$/g, preferably 100 to 200 m$^2$/g (determined in accordance with DIN ISO 9277 (status: 2014 January)).

In addition, it may be advantageous when the silicon-aluminium mixed oxide composition has a dibutyl phthalate value, in g dibutyl phthalate (DBP)/100 g mixed composition, of 300 to 350. The DBP value is a measure of the structure of aggregates. Low values correspond to a low structure, high values to a high structure. The described range of 300 to 350 for the mixed oxide composition according to the invention corresponds to a high structure. In the DBP absorption measurement, the force absorption or the torque (in Nm) of the rotating blades of the DBP measuring device is measured on addition of defined amounts of DBP. For the silicon-aluminium mixed oxide composition, this gives preferably a sharply defined maximum showing a subsequent decrease on addition of a specific amount of DBP. The dibutyl phthalate absorption may be measured for example with a Rheocord 90 instrument from Haake, Karlsruhe. This is done by placing 12 g of the silicon-aluminium mixed oxide powder in a kneading chamber, which is then closed with a lid and dibutyl phthalate metered in through a hole in the lid at a specified addition rate of 0.0667 ml/s. The kneader is operated at a motor speed of 125 revolutions per minute. On reaching the maximum torque, the kneader and the DBP addition switch off automatically. From the amount of DBP consumed and the weight of the particles sample, the DBP absorption is calculated according to: DBP value (g/100 g)=(DBP consumed in g/Weight of powder sample in g)×100.

For industrially operated isomerization using a catalyst that includes the silicon-aluminium mixed oxide composition, a reaction process taking place in one or more fixed-bed reactors is preferred. For liquid-phase reactions, it is also possible to use slurry reactors or trickle-bed reactors. Other reactor types such as fluidized-bed reactors or moving-bed reactors may also be used. In this process, it is necessary for the above-described mixed oxide composition produced by flame hydrolysis or pyrogenically to undergo shaping with the addition of a binder by means of a shaping process known to those skilled in the art, particularly in the form of granules, pellets or shaped bodies such as tablets, cylinders, spheres, strand extrudates or rings. Suitable binders are known to those skilled in the art, for example aluminas, ceramic clays, colloids or else amorphous zeolites.

For shaping, 1% to 20% by weight of the silicon-aluminium mixed oxide composition is first mixed with one of the abovementioned binders and additionally with temporary auxiliaries, for example water, aqueous solutions, water substitutes such as glycols and polyglycols, and optionally further auxiliaries such as fixatives, for example cellulose ethers, and/or plasticizers, for example polysaccharides, and/or pressing agents, for example nonionic wax dispersions. This process may be carried out in devices known to those skilled in the art, for example in a kneader or an intensive mixer. This is followed by the actual shaping, which is carried out by a shaping process such as pelleting, extrusion or dry pressing. Before being fixed in the fixed-bed reactor(s), the shapes/shaped bodies are calcined within a temperature range from 200 to 700° C., resulting in the removal at least of the temporary auxiliaries.

The silicon-aluminium mixed oxide composition may be applied to a support that is inert in respect of the isomerization, for example a support made of metal, plastic or ceramic. If the silicon-aluminium mixed oxide composition is applied to an inert support, the mass and composition of the inert support is disregarded in the determination of the composition of the silicon-aluminium mixed oxide composition.

The process according to the invention is carried out with the above-described silicon-aluminium mixed oxide composition as catalyst in order to isomerize $C_4$ to $C_9$ reactant olefins having an internal double bond, preferably $C_4$ to $C_8$ reactant olefins having an internal double bond, more preferably $C_4$ to $C_6$ reactant olefins having an internal double bond, particularly preferably $C_4$ reactant olefins having an internal double bond, to product olefins having a terminal double bond.

The olefins are not necessarily used in pure form, but in industrially available hydrocarbon mixtures. The isomerization accordingly results in the content of the product olefin increasing in the hydrocarbon mixture alongside a parallel decrease in the content of reactant olefin.

$C_5$ olefins are present in light petroleum fractions from refineries or crackers. Technical mixtures that comprise linear $C_4$ olefins are light petroleum fractions from refineries. $C_4$ fractions from FC crackers or steam crackers, mixtures from Fischer-Tropsch syntheses, mixtures from the dehydrogenation of butanes and mixtures formed by metathesis or from other industrial processes. For example, mixtures of linear butenes suitable for the process according to the invention are obtainable from the $C_4$ fraction of a steam cracker. The first step in this case is removal of butadiene. This is accomplished either by extraction (or extractive distillation) of the butadiene or by selective hydrogenation thereof. In both cases a virtually butadiene-free $C_4$ cut is obtained, referred to as raffinate I. In the second step, isobutene is removed from the $C_4$ stream, for example by production of MTBE through reaction with methanol. The now isobutene-free and butadiene-free $C_4$ cut, referred to as raffinate II, comprises the linear butenes and any butanes. If this then also undergoes removal of at least part of the 1-butene present, the resulting cut is referred to as raffinate III.

In a preferred embodiment, the hydrocarbon mixture fed into the process according to the invention is a $C_4$ olefin-containing stream. Suitable $C_4$ olefin-containing streams are for example the crude butane or the $C_4$ raffinate III. Crude butane is obtained inter alia as a by-product in the oligomerization of $C_4$ olefins. A crude butane in the context of the present invention is, however, any $C_4$ hydrocarbon stream that, in addition to a high proportion of saturated $C_4$ hydrocarbons (typically more than 50% by weight), also comprises linear butenes, the 1-butene content being less than 10% of the total linear butene content. $C_4$ raffinate III is in the context of the present invention obtained after the removal of at least 1,3-butadiene, isobutene and 1-butene from $C_4$ fractions from steam crackers or FCC crackers.

The reactant olefins are olefins according to the invention having an internal double bond that are converted by isomerization at least partially into product olefins, that is to say olefins having a terminal double bond (alpha olefins). In a preferred embodiment, the reactant olefins are cis- and/or trans-2-butenes or hydrocarbon mixtures comprising cis- and/or trans-2-butenes that are converted into 1-butene by the isomerization according to the invention. This allows enrichment of 1-butene in hydrocarbon mixtures previously low in 1-butene in order to make said mixtures usable in value-adding processes, for example for further processing in processes in which high 1-butene concentrations are preferable (e.g. oligomerization or oxidative dehydrogenation to butadiene), for isolation of the 1-butene or for hydroformylation to pentanal.

The conversion of the reactant olefin(s) into product olefin is limited in particular by the temperature-dependent position of the chemical equilibrium of the isomerization reaction. The advantage of using a catalyst of the invention is that the conversion corresponds to the conversion at thermodynamic equilibrium over a broader temperature range or is only marginally lower than this. This applies also to the isomerization of 2-butene to 1-butene, which is limited by the thermodynamic equilibrium of the n-butene isomers. The thermodynamic equilibrium of a mixture comprising 2-butenes and 1-butene is shifted at high temperatures towards 1-butene. The thermodynamic equilibrium for 1-butene at a temperature of 400° C. is approximately between 24% and 25% and at a temperature of 500° C. is approximately 29%.

For the isomerization process according to the invention, it is preferable to use at least one fixed-bed reactor. Other reactor types, such as fluidized-bed reactors, moving-bed reactors, slurry reactors or trickle-bed reactors may also be used.

The process according to the invention may be carried out at atmospheric pressure. Higher reaction pressures may however also be employed. Operation under pressure in the process according to the invention is, for example, useful when the product olefin from the isomerization process according to the invention is being fed into an additional separation step that is likewise operated under pressure. Thus, after undergoing isomerization of 2-butene to 1-butene, the hydrocarbon mixture may be fed into an additional separation step in which 1-butene and 2-butene are separated by distillation under pressure.

The isomerization of 2-butene to 1-butene according to the invention takes place preferably at a temperature of between 20° C. and 600° C., more preferably between 100° C. and 500° C. and further preferably between 200° C. and 450° C. The gas hourly space velocity (GHSV) may be from 2000 to 8000 $h^{-1}$, preferably from 2500 to 4000 $h^{-1}$. The selectivity of the isomerization according to the invention in respect of the product olefin is preferably greater than 90%, more preferably greater than 95% and particularly preferably greater than 98%.

If the activity and selectivity of the catalyst according to the invention declines as a result of carbon deposits on the catalyst, the catalyst is expediently regenerated. An advantageous method of catalyst regeneration is to burn off the carbon deposits on the deactivated catalyst in oxygen-containing gases, preferably in air. It may be expedient here to dilute the air with nitrogen. The catalyst regeneration is generally carried out at temperatures of 350° C. to 600° C., preferably of 400° C. to 450° C. This normally allows the initial activity and initial selectivity of the catalyst according to the invention to be recovered in a simple manner.

The invention is described below with reference to an example. The example serves to elucidate the invention and does not restrict the subject matter of the invention.

Example 1—Isomerization of 2-butene to 1-butene

A tubular reactor having a diameter of 0.6 mm was filled with 0.2 g of a catalyst of the invention (Aerosil® MOX170, approx. 1% by weight of aluminium oxide, BET surface area between 140 and 200 $m^2/g$). The reactor was charged with crude butane having the following composition:

| 1-Butene | cis-2-Butene | trans-2-Butene | Isobutene | n-Butane | Isobutane | Other HC |
|---|---|---|---|---|---|---|
| 1.56 | 8.87 | 20.18 | 0 | 67.9 | 0.53 | 0.86 |

The crude butane was passed through the reactor at varying volume flows. The isomerization took place at a temperature of 380° C. and a pressure in the reactor of 5.7 to 6 bara (bar absolute). In the reaction, the conversions of 2-butene and the selectivities for the formation of 1-butene were determined. The analysis was by gas chromatography. Evaluation was according to peak area by the internal standard method. The internal standard used was n-butane.

TABLE 1

Conversions and selectivities for Example 1

| Vol. flow of crude butane [g/h] | Conversion of 2-butene [%] | Selectivity for the formation of 1-butene [%] |
|---|---|---|
| 7.5 | 24.91 | 87.82 |
| 15.2 | 21.91 | 90.66 |
| 25.2 | 20.51 | 94.44 |

The results show that the catalysts of the invention are very well suited for the isomerization.

The invention claimed is:

1. A process for the isomerization of $C_4$ to $C_9$ reactant olefins having an internal double bond to product olefins having a terminal double bond using a heterogeneous catalyst, the process comprising:
   isomerizing said reactant $C_4$ to $C_9$ olefins using the heterogeneous catalyst at a temperature between 200° C. and 450° C., wherein the catalyst comprises a silicon-aluminium mixed oxide composition, having the following composition:

a) 96% to 99.99% by weight of silicon oxide, calculated as $SiO_2$; and
b) 0.01% to 4% by weight of aluminium oxide, calculated as $Al_2O_3$.

2. The process according to claim 1, wherein the catalyst has the following composition:
a) 98.5% to 99.95% by weight of silicon oxide, calculated as $SiO_2$; and
b) 0.05% to 1.5% by weight of aluminium oxide, calculated as $Al_2O_3$.

3. The process according to claim 1, wherein the silicon-aluminium mixed oxide composition has a BET surface area of 50 to 250 $m^2/g$.

4. The process according to claim 1, wherein the catalyst consists of shaped bodies produced from the silicon-aluminium mixed oxide composition in a forming process with the addition of binders and at least temporary auxiliaries.

5. The process according to claim 1, wherein the isomerization is carried out using a hydrocarbon mixture that comprises the reactant olefin to be isomerized and the product olefin, wherein the content of the product olefin is increased through isomerization.

6. The process according to claim 1, wherein the isomerization is carried out at a gas hourly space velocity from 2000 to 8000 $h^{-1}$.

7. The process according to claim 1, wherein the reactant olefins used are $C_4$ to $C_8$ reactant olefins having an internal double bond.

8. The process according to claim 1, wherein the reactant olefins used are cis-2-butenes, trans-2-butenes, or a hydrocarbon mixture comprising these 2-butenes; and wherein the product olefin having a terminal double bond is 1-butene.

9. The process according to claim 1, wherein the silicon-aluminium mixed oxide composition is predominantly or entirely present in the form of aggregated primary particles.

10. The process according to claim 9, wherein the silicon-aluminium mixed oxide composition, wherein a weight ratio $(Al_2O_3/SiO_2)_{surface}$ of the primary particles in a near-surface region is smaller than a weight ratio $(Al_2O_3/SiO_2)_{total}$ in the totality of the primary particles.

11. The process according to claim 9, wherein the silicon-aluminium mixed oxide composition is predominantly or entirely present in the form of aggregated primary particles in which:
I) a weight ratio of $(Al_2O_3/SiO_2)_{total}$ in the totality of the primary particles is 0.002 to 0.05, and
II) a weight ratio $(Al_2O_3/SiO_2)_{surface}$ of the primary particles in a near-surface layer having a thickness of 5 nm is less than the weight ratio in the totality of the primary particles.

12. The process according to claim 1, wherein the catalyst is completely crystalline, partly crystalline or X-ray amorphous.

13. The process according to claim 12, wherein the catalyst is X-ray amorphous.

14. The process according to claim 1, wherein the silicon-aluminium mixed oxide composition has a BET surface area of 100 to 220 $m^2/g$.

15. The process according to claim 1, wherein the isomerization is carried out at a gas hourly space velocity from 2500 to 4000 $h^{-1}$.

16. The process according to claim 1, wherein the reactant olefins used are $C_4$ reactant olefins having an internal double bond.

17. The process according to claim 11, wherein the weight ratio of $(Al_2O_3/SiO_2)_{total}$ in the totality of the primary particles is 0.005 to 0.01.

* * * * *